United States Patent [19]

Galkin

[11] Patent Number: 5,063,583

[45] Date of Patent: Nov. 5, 1991

[54] METHOD AND APPARATUS FOR TESTING RADIOGRAPHIC FILM PROCESSORS

[75] Inventor: Benjamin M. Galkin, Cherry Hill, N.J.

[73] Assignee: Thomas Jefferson University, Philadelphia, Pa.

[21] Appl. No.: 441,567

[22] Filed: Nov. 24, 1989

[51] Int. Cl.$^5$ ............................................. G01D 18/00
[52] U.S. Cl. .................................. 378/207; 378/182; 378/185; 378/165; 378/167; 378/188
[58] Field of Search ............... 378/185, 182, 187, 188, 378/186, 210, 23, 163, 164, 166, 167, 207, 2, 165, 162, 56, 54; 354/298, 76, 355

[56] References Cited

U.S. PATENT DOCUMENTS

| | | | |
|---|---|---|---|
| 1,973,906 | 9/1934 | Levene et al. | 378/162 |
| 2,505,562 | 4/1950 | Meschan et al. | 378/185 |
| 3,864,038 | 2/1975 | Palazzolo | 378/207 |
| 4,095,111 | 6/1978 | Katz et al. | 378/161 |
| 4,718,757 | 1/1988 | Edwards | 378/210 |
| 4,764,948 | 7/1988 | Hurwitz | 378/165 |
| 4,788,707 | 11/1988 | Malamud et al. | 378/162 |
| 4,860,330 | 8/1989 | Strommer et al. | 378/162 |

FOREIGN PATENT DOCUMENTS 2104252  8/1971  Fed. Rep. of Germany ...... 378/166

OTHER PUBLICATIONS

R. H. Herz, The Photographic Action of Ionizing Radiations, Fundamentals of Radiography, 7.4:274–276.
R. Edward Hendrick, Quality Control in Mammography, Current Opinion in Radiology 1989, 1:203–211.

Primary Examiner—Edward P. Westin
Assistant Examiner—Don Wong
Attorney, Agent, or Firm—Woodcock Washburn Kurtz Mackiewicz & Norris

[57] ABSTRACT

Methods and apparatus for determining film processor performance. Films for use in radiographic imaging, adapted to evaluate performance of a film processor which develops an image of a structure of interest on the films are provided. The films have exposable areas for radiographically imaging the structure of interest, and test means integrally located on the exposable areas for determining the performance of the processor which develops the radiographic image on the film. Additionally, methods of determining performance of film processors which develop radiographic images of structures of interest on films comprise the steps of shielding a first portion of the film from radiographic imaging of the structure of interest, imaging radiographically the structure of interest on a second portion of the film, impressing a test pattern on the first portion of the film, processing the film to develop the test pattern on the first portion of a film and the radiographic image of the structure of interest on the second portion of the film, and determining the performance of the film processor by visually comparing the test pattern to a control pattern. Methods and apparatus provided in accordance with the present invention eliminate the need for independent calibration of film processors that develop radiographic images on X-ray films and are particularly useful for determining the effect of the film processor on the diagnostic quality of mammograms.

25 Claims, 3 Drawing Sheets

METHOD AND APPARATUS FOR TESTING RADIOGRAPHIC FILM PROCESSORS

FIELD OF THE INVENTION

This invention relates generally to the field of radiology. More specifically, this invention relates to methods and apparatus for testing the performance of radiographic film processors which develop radiographic films.

BACKGROUND OF THE INVENTION

Radiographic imaging of body parts is well known and extremely useful as a diagnostic tool in the medical arts. Radiographic imaging involves positioning a part of a patient to be imaged denoted as the "structure of interest" under an X-ray tube, exposing the structure of interest to an X-ray beam, and recording the X-ray image on an image receptor. The receptor in most instances is a radiographic film disposed in contact with an intensifying screen. The film and screen are kept in tight contact during the exposure in a film holder or cassette. After exposing the structure of interest, the film is removed from the cassette, may be labeled with the patient's name and other identifying information, and then developed.

The diagnostic value of radiographic imaging as described above is dependent on the quality of the radiographic image, which in turn depends on an interplay of several factors. One of the more important of these factors is the process by which the radiographic image is developed. Radiographic images which are made on radiographic films are generally developed in devices called "film processors." Film processors are subject to many variations which are functions of the kind of film processor used to develop the film, the age and quality of the chemicals in the film processor which develop the film, the duration of time the film is processed, and the temperature and pH of the chemicals. Since the diagnostic value of a radiographic image is highly dependent upon the quality of the radiographic image, it is imperative that the film processor be well controlled in order to optimally develop the image. It is also important to minimize fluctuation of processor parameters from film to film.

As is known by those with skill in the art, an X-ray image of acceptable diagnostic quality generally comprises an image of the structure of interest as a series of gray levels. Examination of the gray level image indicates whether the structure of interest is healthy, or whether the structure of interest may contain certain diseases such as, for example, cancer.

Since the quality of the radiographic image is highly dependent on the film processor, the film processor must be periodically tested to ensure that the images which are produced have a high diagnostic quality. There are several prior methods currently in use to test film processors. One such method involves the use of a "sensitometer" and a "densitometer." A sensitometer is an instrument which impresses a series of graduated exposures on a photographic material. In these sensitometers, a light source of known luminous intensity is displaced at a fixed distance from an exposure plane and emits radiation of known spectral intensity. The surface of the photographic material is positioned to substantially coincide with the exposure plane.

In the sensitometer, an exposure modulating device is located between a film and the light source. If the exposure modulating device is removed, the entire photosensitive material may be uniformly illuminated. However, the purpose of the exposure modulating device is to alter this condition so that various areas of the photosensitive surface are subjected to a series of different exposures, thereby forming a graded density pattern on the photosensitive surface which is developed as a series of gray levels. This density pattern is a function of the type of film and the action of the processor.

After the film is developed by a film processor with the sensitometric graded density gray scale level pattern imposed thereon, a densitometer is used to measure densities created by the exposure modulated device. In this fashion, the graded density pattern, which may be precalibrated in terms of various parameters such as for example, film speed, base and fog, and contrast, can be used to gauge and evaluate the performance of the film processor.

Various other methods and apparatus have been used to test film processors. Examples of these other methods and apparatus are sensitometric film strips which have been pre-exposed and aged, and are then packaged to be sold commercially. These pre-exposed strips are used in conjunction with a readout device. To check the film processor, one of the strips is developed and inserted into the readout device. When the film is withdrawn, the readout device produces a light signal which indicates the temperature and the condition of the chemicals in the processor. No digital readout is provided and no quantitative indications of the condition of the film processor can be determined.

Methods to check film processors by measuring the pH of the chemicals and the operating temperature of the film processor are also known in the art. It has also been known to use "step wedges" to create a graded pattern on radiographic films. These step wedges are generally constructed of an X-ray absorbing material and are used to determine the effect that the X-rays have on the image quality, but not the effect that the film processor has on the image quality.

The aforementioned prior methods for testing a film processor which develops radiographic images do not satisfy long-felt needs in the art for methods and apparatus to test film processors that are quick, efficient and standardized to particular exposures and film types. The recommended frequency for conducting sensitometric and densitometric tests is daily. However, in the realities of the clinical environment, daily testing of film processors is often not completed.

There are many reasons that daily testing is not always accomplished. Chief among these reasons are that special training and equipment are needed, and additional X-ray film is required. As a result, the diagnostic quality of X-ray images is often severely compromised. Poor film processor performance results in degraded radiographic image quality and could ultimately result in failure to detect diseases. This is particularly devastating, for example, in radiographic images of female breasts called "mammograms" where diagnostic features are often subtle, and early detection of breast cancer is often critical to future survival.

The inventor of the subject matter herein claimed and disclosed has recognized a long-felt need in the art to eliminate the need for repeat densitometric readings of test films to monitor the performance of film processors. There are further long-felt needs in the art to minimize the use of extra test films to monitor processor performance, and also to provide the ability to record the effect of processing on the radiographic image for recall during subsequent examinations. A permanent record of processor monitoring for quality assurance and medico-legal needs is also desired in the art.

SUMMARY OF THE INVENTION

The aforementioned long-felt needs are satisfied by methods and apparatus provided in accordance with the present invention. In preferred embodiments, a film for use in radiographic imaging, adapted to evaluate performance of a film processor which develops an image of a structure of interest on the film comprising an exposable area for radiographically imaging a structure of interest, and test means integrally located on the exposable area for determining the performance of the processor which develops the radiographic image on the film is provided.

In still further preferred embodiments, methods of determining performance of a film processor which develops a radiographic image of a structure of interest on a film are provided in accordance with the present invention. The methods comprise the steps of shielding a first portion of the film from radiographic imaging of the structure of interest, imaging radiographically the structure of interest on a second portion of the film, impressing a test pattern on the first portion of the film, processing the film to develop the test pattern on the first portion of the film and the radiographic image of the structure of interest on the second portion of the film, and determining the performance of the film processor by visually comparing the test pattern to a control pattern.

DETAILED DESCRIPTION OF PREFERRED EMBODIMENTS

Figure 1A:
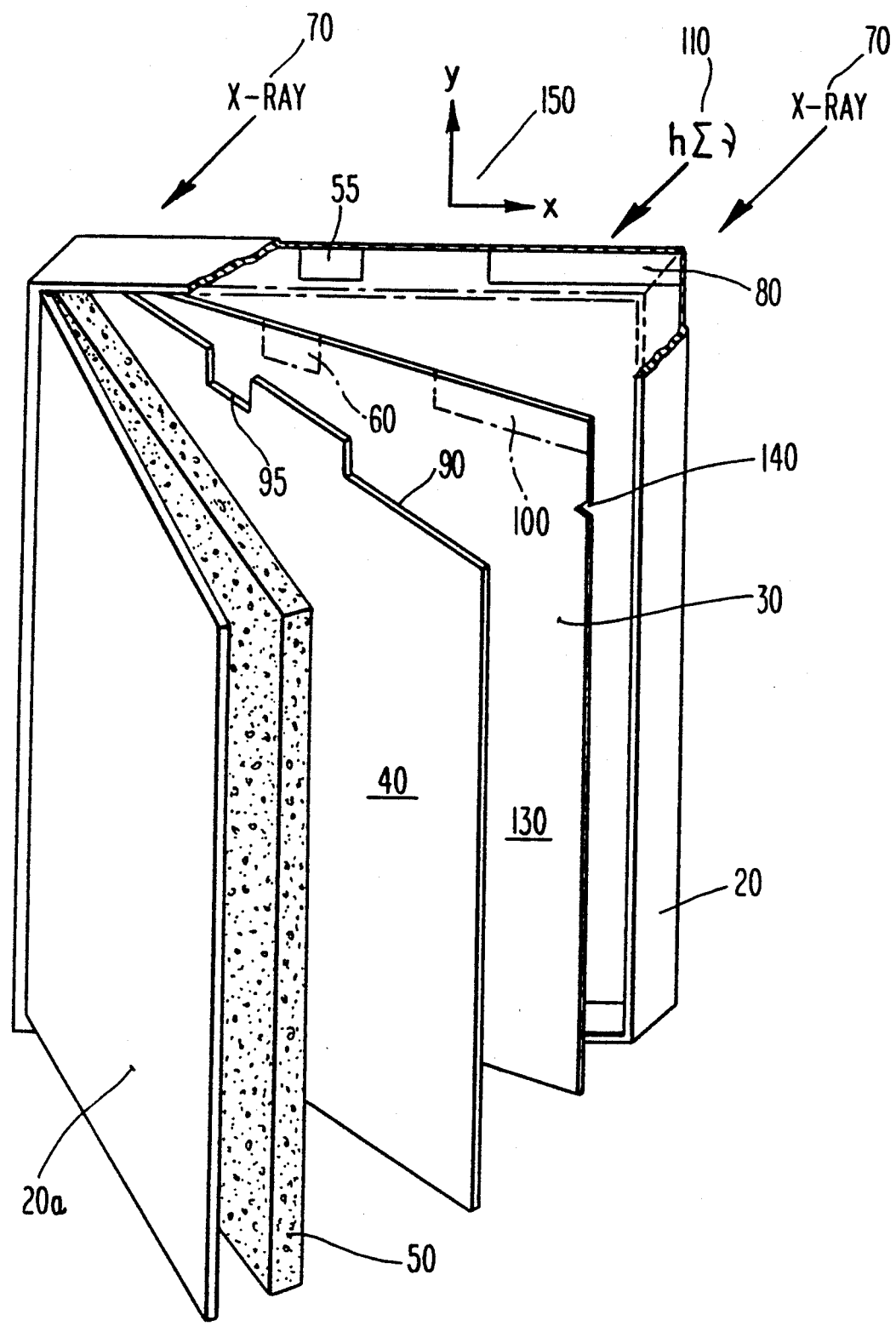
FIGS. 1A and 1B are isometric views of cassettes provided in accordance with the present invention for holding radiographic films.

Referring now to the drawings wherein like reference numerals refer to like elements, in FIG. 1A a cassette holder having a front cover 20 and back cover 20a provides a housing for the film 30. The film 30 is generally a type of radiographic imaging film. In preferred embodiments, a silver halide emulsion coats a first side of the film 30 and absorbs radiation to form an image of a structure of interest on film 30.

Means for intensifying X-rays 40 is provided to the cassette. Intensifying means 40 is generally a screen that is placed in cooperative relationship with radiographic film 30 to intensify the X-rays, shown at 70, which carry information about the structure of interest. Intensifying screen 40 fluoresces when X-rays 70 impinge on it such that the fluorescent radiation forms an image of the structure of interest on film 30. In preferred embodiments, film 30 is a single emulsion film for use in mammography. Thus, the structure of interest is a human breast. Since a single emulsion film is used in mammography, only one intensifying screen 40 is provided to the cassette. However, in other radiographic imaging techniques where double emulsion films are typically used, two intensifying screens are provided to the cassette. In describing the invention hereinafter, reference will be made to single emulsion radiographic films for use in mammography wherein the structure of interest is a human breast and the cassettes therefore have a single intensifying screen.

In further preferred embodiments, a pressure pad 50 is placed in the cassette in cooperative relation with intensifying screen 40 so that when the cassette is closed, intensifying screen 40 fits snugly against film 30 during X-ray imaging of the breast. Means 55 for allowing codable information to identify the patient to be impressed on film 30 is integrally formed on front cover 20. Codable means 55 provides for an area 60 on film 30 wherein identifying information of the patient can be impressed on film 30. Codable means 55 blocks X-rays so that coding area 60 is not impressed with a radiographic image during imaging of the breast. Preferably, the identifying information is impressed photographically on coding area 60 after the breast is imaged.

Similarly, means 80 for blocking X-rays 70 is integrally mounted on front side 20 and interfaced with a first portion 100 of film 30 to block X-ray energy from reaching the first portion 100 of film 30. In this fashion after X-rays 70 have irradiated film 30, the silver halide emulsion which exists on the first portion 100 of the film has not been irradiated and remains pristine. Furthermore, intensifying screen 40 does not fluoresce radiation onto first portion 100 since X-rays are blocked from reaching screen 40 in an area corresponding to the first portion 100. Thus, other information may be impressed on the first portion 100 of the film 30, rather than the information about the breast which has been carried by X-rays 70 to a second portion 130 of film 30.

Since the first portion 100 of film 30 and coding area 60 are not to be impressed with radiographic images of the breast, the intensifying screen 40 is cut out at 90 and 95 corresponding to areas on film 30 substantially equal to the area of the first portion 100 and coding area 60 respectively. Since it is desired that no fluorescent energy reaches the first portion 100 of film 30 and area 60, cutouts 90 and 95 in intensifying screen 40 are provided to ensure that no florescent energy reaches the first portion of the film 100 and area 60.

Figure 1B:
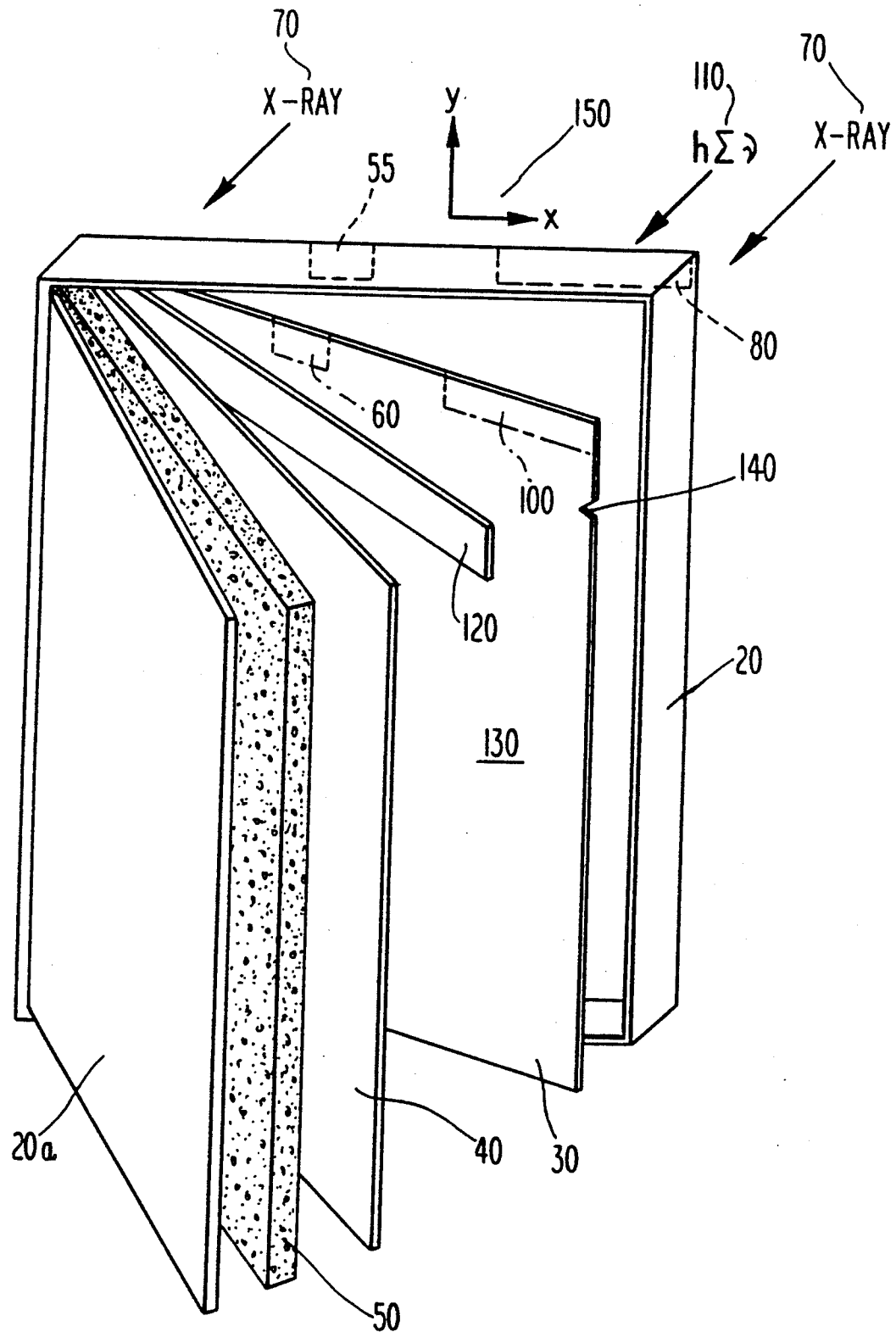

Other means may be provided to the cassette to ensure that area 60 and first portion 100 are not impressed with radiographic images during breast imaging. Referring to FIG. 1B, light blocking means 120 is provided to the cassette disposed between intensifying screen 40 and film 30. Light blocking means 120 is generally a strip of opaque material having approximately the same extent in the X and Y directions as area 60 and first portion 100. Light blocking means 120 prevents florescent energy from reaching area 60 and first portion 100, or more specifically, the space on film 30 corresponding to the area of light blocking means 120.

In yet further preferred embodiments, intensifying screen 40 could simply be made smaller than film 30 so that area 60 and first portion 100 are not illuminated with florescent energy from the screen. Alternatively, an X-ray blocker could be integrally formed in holder 20 to prevent X-rays 70 from reaching areas on screen 40 corresponding to area 60 and first portion 100. An X-ray blocker of this sort preferably comprises a thin sheet of lead which absorbs the X-rays.

The first portion 100 of film 30 is adapted to receive a graded density test pattern which acts as a test means to determine the performance of the film processor that develops the mammogram on second portion 130 of film 30. The graded density pattern is impressed on the first portion 100 of film 30 by a standard sensitometric technique. After the radiographic image has been impressed on second portion 130, film 30 is removed from the cassette in a darkroom so that the graded density pattern can be impressed on first portion 100. Similarly, identifying information for the patient is photographically impressed on coding area 60 after film 30 has been removed from the cassette.

During impression of the graded density test pattern on first portion 100, light having a known spectral content, shown generally at 110, irradiates the film on first portion 100. The light 110 is multifrequency, having energy equal to $h\Sigma\nu$ signifying radiant energy associated with a range of frequencies. The light 110 is generally emitted from a sensitometer having first been modulated by an exposure modulating device (not shown) and therefore, has a known spectral intensity corresponding to the various frequencies in light 110. A graded density test pattern is thus impressed on film 30 in first portion 100.

In still further preferred embodiments of the cassette provided in accordance with the present invention, the X-ray blocking means 80 and codable means 55 are comprised of a material which absorbs X-rays, thereby preventing the X-rays from reaching intensifying screen 40. Various types of polymer plastics, absorbing foils, or other radiant energy absorbers may thus be used to form X-ray blocking means 80 and codable means 55. Similarly, light blocking means 120 is also constructed of a material which can absorb light comprising multifrequencies.

A graded density test pattern is impressed on the first portion 100 of film 30 by light of known spectral content 110. Thus, film 30 will have essentially two types of useful images impressed thereon. The first image is the standard radiographic image of a structure of interest on the second portion 130 of film 30 called a mammogram. The other image is formed on the first portion 100 of film 30, and is a graded density pattern which is used to test and evaluate the performance of the film processor.

The graded density test pattern is generally a sensitometric image whose development is highly dependent upon the parameters which affect the film processor. Thus, it is possible to use the graded density test pattern to evaluate the film processor's performance independently of other factors that effect the image of the structure of interest, and to ensure that the mammogram formed on the second portion 130 of film 30 is a high quality image that is useful for diagnostic purposes.

It is generally desired to provide means 140 interfaced with film 30 to identify film type. There are many types of radiographic films which can generally be used to form radiographic images. Depending on the type of film used, the film processor will develop the film and produce images whose gray scale is also dependent on film type corresponding to particular radiographic needs.

In yet further preferred embodiments, means 140 for identifying film type is simply a "notch" which is cut out of film 30, and placed in a preferred orientation on film 30. A cartesian coordinate system 150 indicates that notch 140 is oriented along the long edge of film 30. In other preferred embodiments, notch 140 could be oriented along the narrow edge of the film. As is conventional, when film 30 is held in the right hand and notch 140 is in the upper right hand corner, the emulsion side of film 30 faces the individual holding film 30. There may be a single notch, or a series of notches of various shapes cut into film 30 to indicate the particular film type.

Figure 2A:
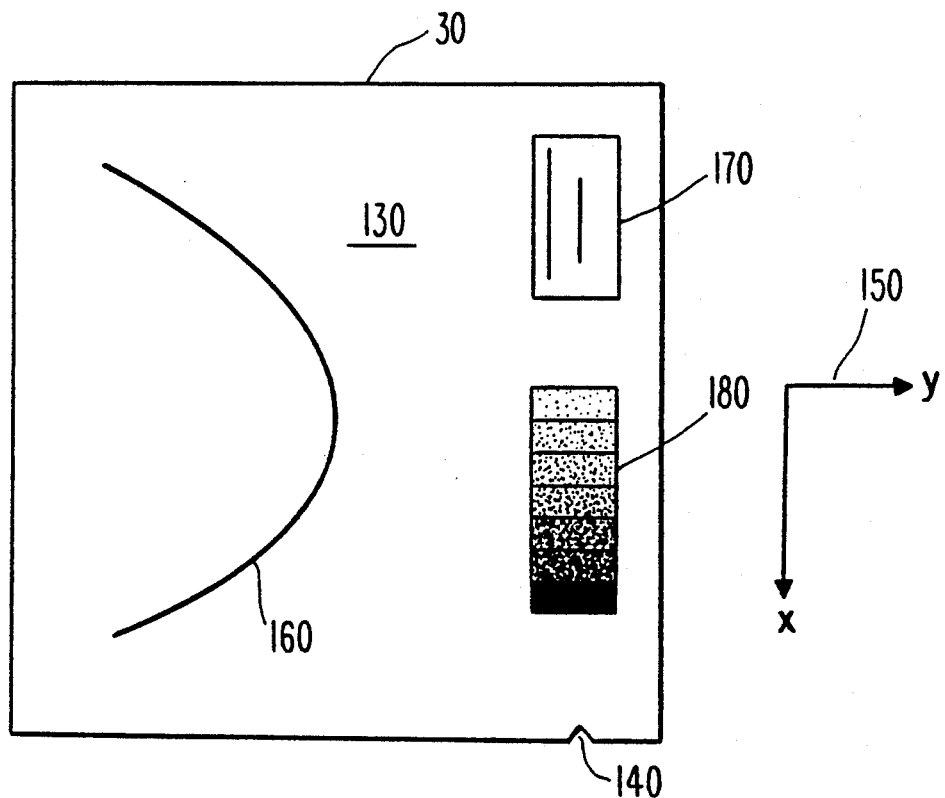
FIGS. 2A and 2B are schematics of radiographic films provided in accordance with the present invention.

Referring to FIG. 2A, a radiographic image, herein a mammogram, is shown at 160. As is known by those with skill in the art, female breasts are subject to a particularly devastating form of cancer which, if detected early, may be curable with a high success rate. Thus, high quality mammograms are desired in the radiographic imaging art to allow radiological physicians and professionals to make early and accurate diagnoses of breast cancer.

The film 30 generally comprises an exposable area which is coated with a silver halide emulsion. The exposable area, corresponding to first portion 100, area 60 and second portion 130 in FIGS. 1A and 1B, has impressed thereon various images including mammogram 160, coding area 170 for identifying the patient, and test means 180 which is generally a graded density test pattern that has been sensitometrically produced. In preferred embodiments, coding means 170 may be photographically produced, but it could simply be mechanically attached to the exposable area of film 30. Notch 140 indicates the film type, and is oriented in a preferred direction along an edge of the film.

Figure 2B:
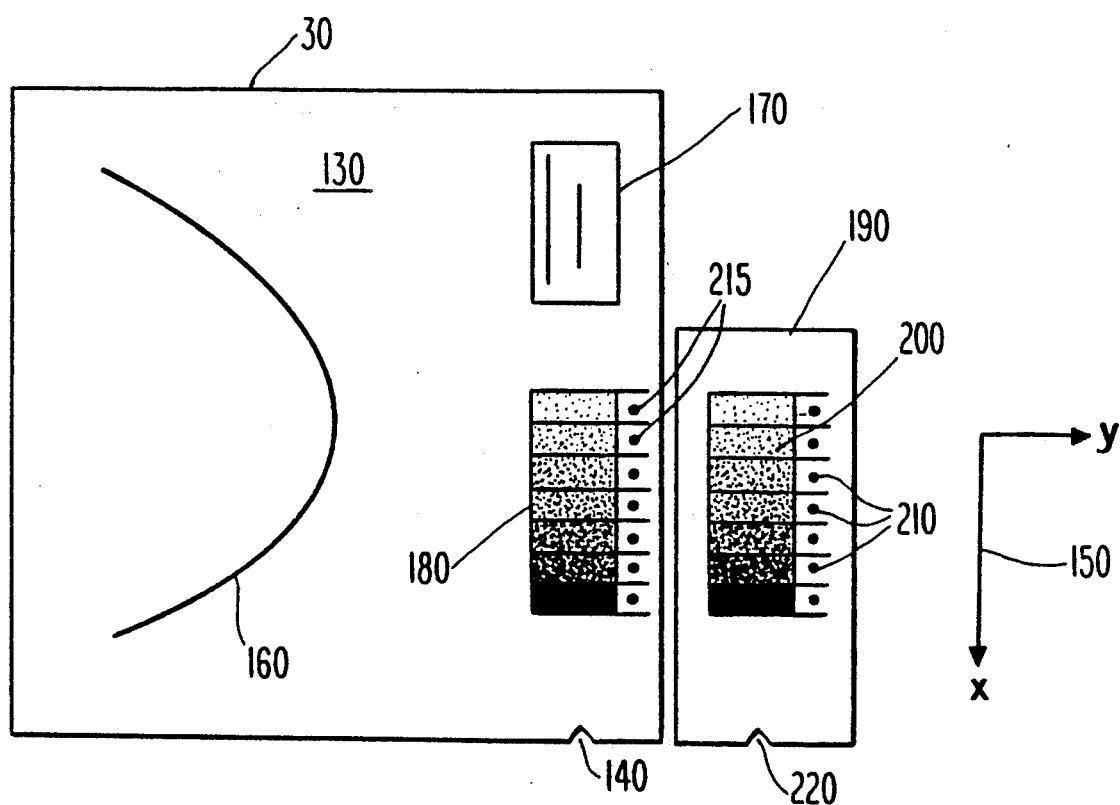

As is illustrated in FIGS. 2A and 2B, graded density test pattern 180 in preferred embodiments is a series of gray levels impressed on film 30. Referring to FIG. 2B, a control film 190 is placed in a proximate position to film 30 so that a control pattern 200 impressed on control film 190 can be compared to graded density test pattern 180 impressed on film 30. In preferred embodiments, control pattern 200 is also a graded density pattern.

In accordance with the present invention, control density pattern 200 impressed on control film 190 is held in position while film 30 having graded density test pattern 180 and mammogram 160 imposed thereon is placed in a proximate position to control film 190 so that graded density test pattern 180 and control density pattern 200 can be visually compared. Variations from accepted norms of graded density test pattern 180 as compared to control pattern 200 may then be visually noted by comparing step markers 210 on control film 190 to step markers 215 on film 30, thereby indicating the quality by which the film processor has developed mammogram 160 on film 30. Step markers 210 and 215 correspond to the various gray levels in control density pattern 200 and graded density test pattern 180, respectively.

Markers 210 provide an indication of what parameters have been measured, for example, film speed, base and fog, and contrast. Control density pattern 200 is calibrated to provide a gray scale indication of a film processor that is considered to be performing optimally in developing radiographic images. By lining up the gray levels on test pattern 180 to the corresponding gray levels on control pattern 200, the difference between step markers 215 and step markers 210 can be noted. Step markers 215 and 210 may be numbers corresponding to gray levels, or generally any type of standardized symbols that provide an indication of the magnitude of the gray levels. The difference between the step markers 215 and 210 after the gray levels on graded density test pattern 180 and control density pattern 200 have been matched provides an indication of how the film processor is performing, and therefore the diagnostic quality of mammogram 160.

Radiographic films provided in accordance with the present invention eliminate the need for complex, frequent densitometric tests of film processors. Thus radiographic films and control films provided in accordance with the present invention eliminate costly, independent densitometric tests of radiographic films to determine film processor performance, and greatly streamline the testing process for the film processor. No inaccuracies in determining performance of film processors is engendered through the use of methods and apparatus provided in accordance with the present invention because a human eye can detect differences in density of at least 0.05. This is well within the accepted requirements for analyzing sensitometric graded density patterns to determine film processor efficiency and performance.

In accordance with the present invention, notch 220 is physically cut from control film 190 to determine the control film type. By comparing notch 220 with notch 140, the radiologist can ensure that the same type of film which is used in constructing mammogram 160 is used to provide the control density pattern 200.

Methods and apparatus provided in accordance with the present invention are generally useful for both dedicated and non-dedicated film processors. A "dedicated" film processor is one that is used exclusively for developing a single type of radiographic image such as a mammogram. However, most film processors are "non-dedicated" because they are used to develop a number of different kinds of radiographic images including mammograms. Since control film 190 is precalibrated to represent an optimal film processor, it is useful in determining the performance of both dedicated and non-dedicated film processors. Thus, methods and apparatus for testing both dedicated and non-dedicated film processors provided in accordance with the present invention solve long-felt needs in the art for efficient and cost-effective tests to ensure that mammograms and other radiographic images are of the highest quality for diagnostic purposes. These needs have not been satisfied by methods and apparatus which have existed prior to the invention herein claimed and disclosed.

There have thus been described certain preferred embodiments of methods and apparatus for testing radiographic film processors. While preferred embodiments have been disclosed and described, it will be recognized by those with skill in the art that modifications are within the true spirit and scope of the invention. The appended claims are intended to cover all such modification.

What is claimed is:

1. A method of determining performance of a film processor which develops a radiographic image of a structure of interest on a film having an emulsion, comprising the steps of:
   shielding a first portion of the film along one edge of the film from x-ray energy used for imaging of the structure of interest, which edge is furthest from the structure of interest;
   impressing a first calibrated test pattern on the first portion of the film, said first pattern comprising a first calibrated graded stepwise density pattern having density positions, said density pattern produced by visible light, and a first plurality of symbols, located adjacent said first calibrated graded density pattern, wherein each symbol indicates the magnitude of one of said density positions;
   providing a control film of similar emulsion as the emulsion of said film;
   impressing a second calibrated test pattern along one edge of said control film said second calibrated test pattern comprising a second calibrated graded stepwise density pattern having density positions, said density pattern produced by visible light, and a second plurality of symbols, located adjacent said second calibrated graded density pattern, wherein each symbol indicates the magnitude of one of said density positions, wherein the step of impressing said first calibrated test pattern and said second calibrated test pattern are identical;
   processing the film in a film processor to develop the first calibrated test pattern on the first portion of the film and the radiographic image of the structure of interest on the second portion of the film;
   processing said control film to develop the second calibrated test pattern; and
   measuring the performance of the film processor used to develope the film by visually comparing and noting the symbols associated with those density positions between the first calibrated test pattern on the film and the second calibrated test pattern on the control film which match.

2. The method recited in claim 1 further comprising the step of coding the film on the first portion to identify the patient.

3. The method recited in claim 2 wherein the coding step is a photographic coding step.

4. The method recited in claim 1 wherein the second calibrated density pattern is precalibrated in terms of a plurality of parameters.

5. The method recited in claim 4 wherein the plurality of parameters is determined by densitometric analysis.

6. The method recited in claim 5 further comprising the step of identifying the film type and the control film type.

7. The method recited in claim 6 wherein the identifying step further comprises the steps of:
   comparing a first means for identifying film type formed on the film with a second means for identifying film type formed on the control film to ensure that the film and control film are of similar emulsion.

8. The method recited in claim 7 wherein the first means for identifying film type and the second means for identifying film type comprise at least one notch each oriented in a preferred direction.

9. The method recited in claim 7 wherein the radiographic image is a mammogram.

10. A system for evaluating the performance of a radiographic imaging film processor, said system comprising:
    a radiographic imaging film of a first emulsion, comprising an exposable area for imaging a structure of interest using x-rays and a first calibrated graded density pattern impressed by light on a second area of said film, said second area being shielded from the effects of x-rays during imaging of the structure of interest; and
    a control film of a second emulsion, wherein said first and second emulsions are identical, said control film having a light induced second calibrated control density pattern, wherein the performance of the film processor which develops the radiographic image on the film is measured by comparing said first and second calibrated density patterns.

11. The system recited in claim 10 wherein the first calibrated graded density pattern is created from modulated light of known spectral characteristics.

12. The system recited in claim 10 wherein the calibrated control density pattern is photographically imaged on the control film.

13. The system recited in claim 12 wherein the calibrated control density pattern is precalibrated in terms of a plurality of parameters.

14. The system recited in claim 13 wherein the plurality of parameters is determined by densitometric analysis.

15. The system recited in claim 12 wherein the radiographic imaging film further comprises a first identifying means for identifying film type and wherein the control film further comprises second identifying means for identifying film type wherein said first and second identifying means serve to ensure that the film and the control film are of a same type.

16. A single emulsion film for use in mammography and adapted to evaluate changes in film fog, speed or contrast resulting from changes in the performance of a film processor which develops said film, said film comprising:
   a first area for imaging a structure of interest using x-rays; and
   calibrated test means, integrally located in a second area shielded from x-rays, for measuring the performance of the film processor which develops a radiographic image on the film, wherein said second area is located along an edge of said film and wherein said calibrated test means comprises a calibrated graded density pattern produced by visible light and positioned along said edge and a plurality of symbols, located adjacent said calibrated graded density pattern, wherein each symbol indicates the magnitude of a portion of said calibrated graded density pattern.

17. The film recited in claim 16, wherein the calibrated test means is impressed on said second area by visible light from a sensitometer.

18. The film of claim 16, further comprising at least one notch cut in said film in a predetermined orientation to identify type of emulsion of said film.

19. A cassette for housing a single emulsion film during exposure to x-radiation in mammography to image a structure of interest on said film, said cassette comprising:
   a housing, having a front tube side and a back side;
   a single emulsion film disposed within the housing adjacent to said front tube side, wherein said single emulsion defines an emulsion surface, said film having a calibrated graded density pattern and a plurality of symbols located adjacent said calibrated graded density pattern impressed by light in a first film portion along one edge of said film, wherein each symbol indicates the magnitude of a part of said calibrated graded density pattern, said edge being farthest from the structure of interest during exposure;
   a single intensifying screen, disposed within said housing, said screen facing and pressed against said emulsion surface, for irradiating a second film portion with florescent energy induced by x-ray energy, thereby impressing an image of the structure of interest on the second film portion;
   first means for blocking x-ray energy from reaching said first film portion; and
   second means for maintaining the film in contact with said intensifying screen when said cassette is closed.

20. The cassette recited in claim 19 wherein the intensifying screen further allows the calibrated graded density pattern to be impressed by light on the first portion of the film.

21. The cassette of claim 19, wherein said first means for blocking x-ray energy, blocks x-ray energy from reaching a portion of one edge of the intensifying screen.

22. The cassette of claim 19, wherein said housing, said intensifying screen and said film are rectangularly shaped and wherein said first film portion is located along a long edge of said film, said edge being furthest from the structure of interest.

23. The cassette of claim 22, wherein said intensifying screen is substantially co-extensive with said film.

24. The cassette of claim 22, wherein the area of said intensifying screen is smaller than said film so as to prevent production of florescent radiation that could reach said first film portion.

25. The cassette of claim 22, wherein the single intensifying screen further comprising an opaque strip located along a long edge of said screen to block florescent energy, induced by x-ray energy, from reaching said first film portion.

* * * * *